(12) United States Patent
Mullaney et al.

(10) Patent No.: US 11,801,073 B2
(45) Date of Patent: Oct. 31, 2023

(54) SPINAL ALIGNMENT SYSTEM WITH THERMALLY ACTUATED COMPONENT

(71) Applicant: TETRAVISION, LLC, Beacon, NY (US)

(72) Inventors: Michael W. Mullaney, Naples, FL (US); Daniel Moran, Beacon, NY (US)

(73) Assignee: TETRAVISION, LLC, Beacon, NY (US)

( * ) Notice: Subject to any disclaimer, the term of this patent is extended or adjusted under 35 U.S.C. 154(b) by 0 days.

(21) Appl. No.: 17/673,451

(22) Filed: Feb. 16, 2022

(65) Prior Publication Data

US 2022/0257288 A1 Aug. 18, 2022

Related U.S. Application Data

(60) Provisional application No. 63/150,059, filed on Feb. 16, 2021.

(51) Int. Cl.
*A61B 17/70* (2006.01)
*A61B 17/00* (2006.01)

(52) U.S. Cl.
CPC . *A61B 17/7017* (2013.01); *A61B 2017/00411* (2013.01); *A61B 2017/00539* (2013.01)

(58) Field of Classification Search
CPC ...... A61B 17/7017; A61B 2017/00411; A61B 2017/00539; F15B 1/00; F15B 1/02; F15B 7/001; F15B 7/003; F15B 2201/21; F15B 2211/30505; F15B 2211/7051

USPC .................................................. 606/246, 279
See application file for complete search history.

(56) References Cited

U.S. PATENT DOCUMENTS

| | | | |
|---|---|---|---|
| 6,692,495 B1 * | 2/2004 | Zacouto | A61F 2/4425 606/279 |
| 8,092,499 B1 * | 1/2012 | Roth | A61B 17/7017 606/279 |
| 11,304,729 B2 * | 4/2022 | Pool | A61B 17/7004 |
| 2006/0189985 A1 | 8/2006 | Lewis | |
| 2009/0281542 A1 * | 11/2009 | Justis | A61B 17/7017 606/192 |
| 2009/0306717 A1 * | 12/2009 | Kercher | A61B 17/7011 606/279 |
| 2011/0060336 A1 | 3/2011 | Pool et al. | |
| 2011/0196371 A1 | 8/2011 | Forsell | |
| 2011/0301645 A1 * | 12/2011 | Connor | A61B 17/7016 606/246 |
| 2016/0183994 A1 | 6/2016 | Quach et al. | |
| 2021/0259748 A1 | 8/2021 | Mullaney et al. | |
| 2021/0267643 A1 * | 9/2021 | Simpson | A61B 17/7037 |

OTHER PUBLICATIONS

PCT International Search Report and Written Opinion dated May 3, 2022 issued in PCT International Application No. PCT/US2022/016628.

* cited by examiner

*Primary Examiner* — Eduardo C Robert
*Assistant Examiner* — David C Comstock
(74) *Attorney, Agent, or Firm* — Amster, Rothstein & Ebenstein LLP

(57) ABSTRACT

A spinal adjustment system including at least one thermally actuated pump element.

24 Claims, 12 Drawing Sheets

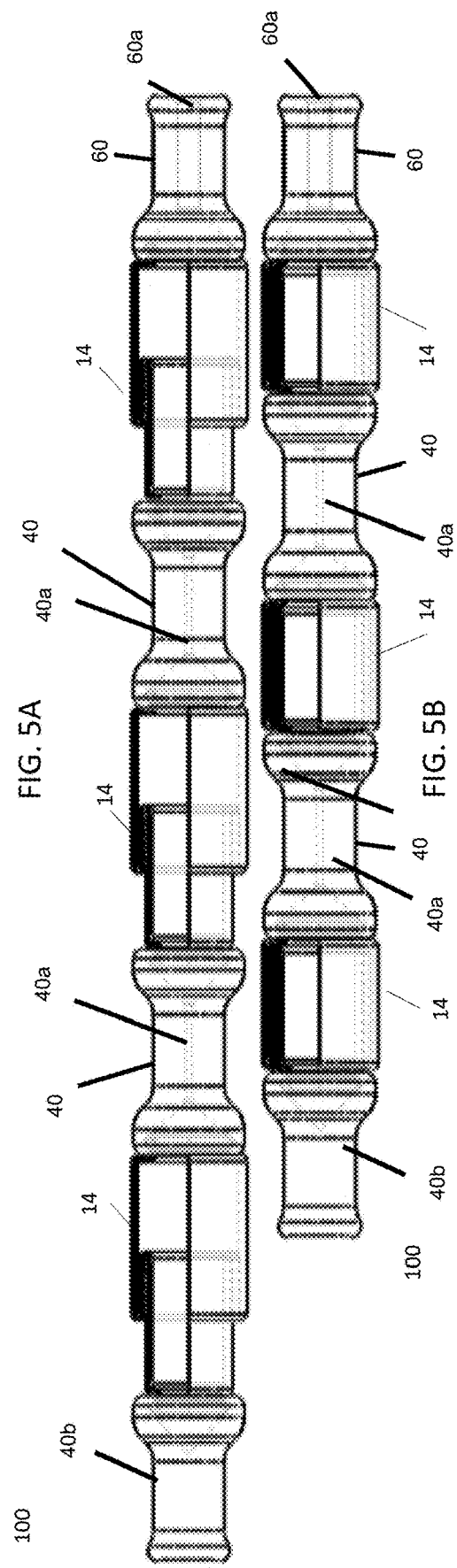

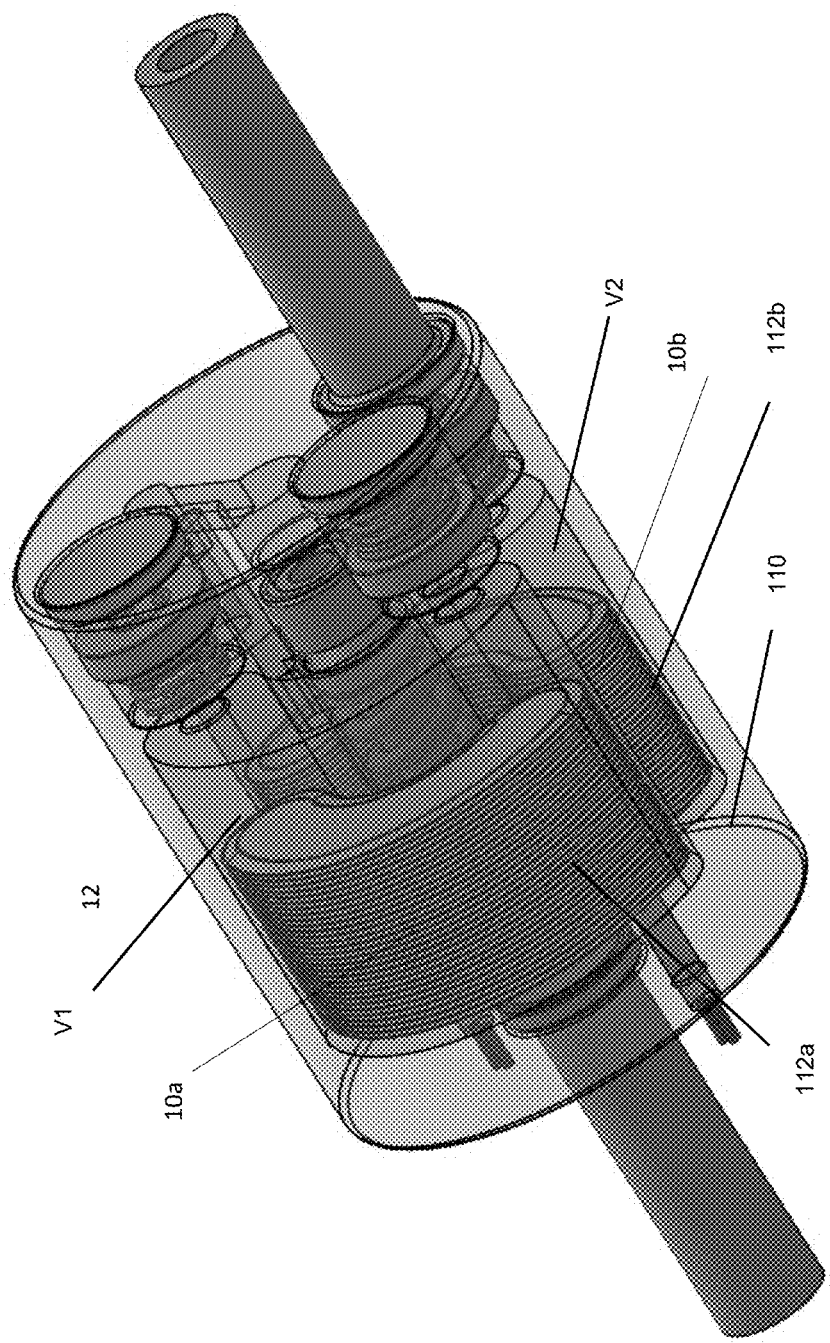

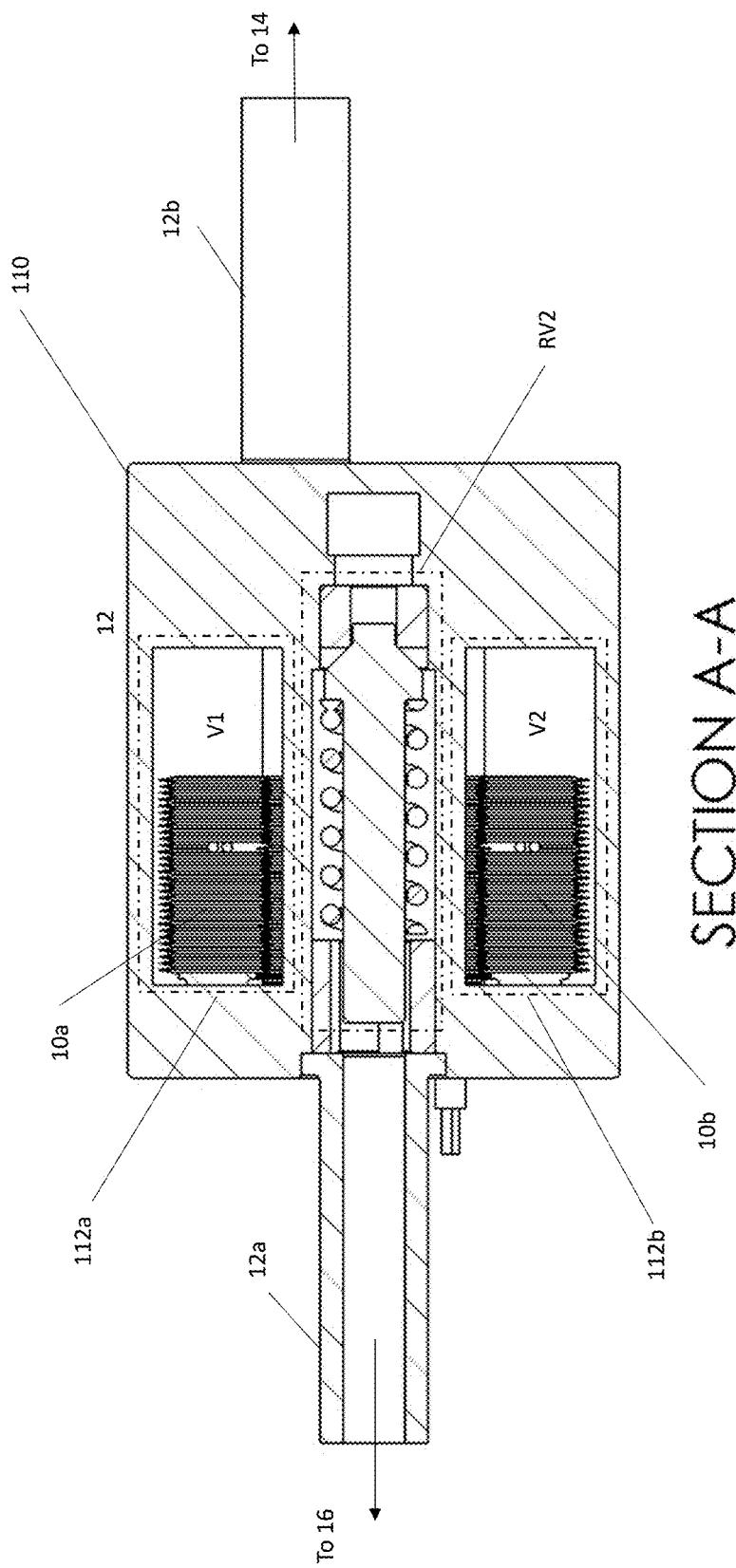
FIG. 8 SECTION A-A

SECTION C-C

SPINAL ALIGNMENT SYSTEM WITH THERMALLY ACTUATED COMPONENT

CROSS-REFERENCE TO RELATED APPLICATIONS

The present application claims benefit of and priority to U.S. Provisional Patent Application Ser. No. 63/150,059, filed Feb. 16, 2021, entitled SPINAL ALIGNMENT SYSTEM WITH THERMALLY ACTUATED COMPONENT, the entire content of which is hereby incorporated by reference herein.

The present application is related to U.S. Nonprovisional patent application Ser. No. 17/176,732, filed Feb. 16, 2021 entitled BIDIRECTIONAL THERMALLY ACTUATED COMPONENT FOR USE IN MEDICAL DEVICES, the entire content of which is hereby incorporated by reference herein.

BACKGROUND

Field of the Disclosure

The present invention relates to a spinal alignment system including thermally actuated actuator components.

Related Art

There are a variety of medical devices and equipment that are used to drive, correct, or maintain alignment, including spinal alignment. Many conventional devices are limited to manually actuated adjustment elements. Reliance on human mechanical intervention risks failure when the user fails to make the appropriate adjustment or makes an improper adjustment. Other devices that use automated adjustment are usually complex and susceptible to error, including runaway catastrophic error.

Accordingly, it would be desirable to provide an alignment system that resolves these and other problems.

SUMMARY

It is an object of this invention to provide a spinal alignment system that is safe and has a limited output relative to input such that the output of the component is finite limiting the danger of gross or catastrophic error.

In embodiments, a spinal alignment system in accordance with an embodiment of the present disclosure includes one or more bidirectional thermally actuated actuator components that may use a material that transitions between solid and fluid based on temperature and may be as harmless as crayon material or paraffin wax, to name a few.

In embodiments, the system, may include feedback information regarding operation of the system to confirm that a given input resulted in a correct output.

A spinal alignment system in accordance with an embodiment of the present disclosure includes: a rolling bladder configured to expand from a retracted state to an extended state and from the extended state back to the retracted state; and a pump connected to the rolling bladder and configured to provide a working fluid to the rolling bladder such that the rolling bladder extends to the extended state, and to remove working fluid from the rolling bladder such that the rolling bladder retracts to the retracted state; the pump including: a first volume filled with the working fluid; a first pump element mounted in the first volume and operable to expand when activated to pump the working fluid out of the first volume; a second volume filled with the working fluid; a second pump element mounted in the second volume and operable to expand when activated to pump the working fluid out of the second volume; wherein the rolling bladder is in fluid communication with the first volume and the second volume and expands to the expanded state when working fluid flows into the rolling bladder and to retract when the working fluid flows out of the rolling bladder; an accumulator in fluid communication with the first volume and the second volume; a power source electrically connected to the first pump and the second pump, and operable to selectively provide power to the first pump and the second pump; wherein, the first pump element expands when power is provided to the first pump element to increase pressure in the first volume to pump the working fluid from the first volume into the rolling bladder such that the rolling bladder expands to the extended state; and wherein, the second pump element expands when power is provided to the second pump element to increase pressure in the second volume to pump working fluid from the second volume into the accumulator and retracts when power is removed from the second pump element such that fluid drains from the rolling bladder into the second volume and the rolling bladder retracts to the retracted state.

In embodiments, the system includes: a first check valve positioned between the first volume and the rolling bladder and configured to control flow of working fluid from the first volume to the rolling bladder; a second check valve positioned between the first volume and the accumulator and configured to control flow of working fluid between first volume and the accumulator; a third check valve positioned between the second volume and the rolling bladder and configured to control flow of working fluid from the rolling bladder to the second volume; and a relief valve position between the second volume and the accumulator and configured to control flow of working fluid from the second volume to the accumulator.

In embodiments, the first check valve allows working fluid to flow from the first volume to the rolling bladder when the first pump element expands and prevents working fluid from flowing back into the first volume when the first pump retracts after power is removed.

In embodiments, the second check valve allows working fluid to flow from the accumulator into the first volume when the first pump element retracts after power is removed.

In embodiments, the relief valve is configured to allow working fluid to flow from the second volume to the accumulator when the second pump element expands when power is applied to the second pump element.

In embodiments, the third check valve is configured to allow the working fluid to flow from the rolling bladder to the second volume such that the rolling bladder returns to the retracted state when the second pump retracts after power is removed.

In embodiments, the power supply is a wire coil.

In embodiments, the system includes power supply circuitry configured to selectively provide power to one of the first pump element and the second pump element.

In embodiments, the power supply circuitry includes: a first diode positioned between the wire coil and the first pump element such that power is provided to the first power pump when current is induced in the wire coil using a rectified sinusoidal signal having a first polarity; and a second diode positioned between the wire coil and the second pump element such that power is provided to the second power pump when current is induced in the wire coil using a rectified sinusoidal signal having a second polarity, opposite the first polarity.

In embodiments, the wire coil is paired with an external wire coil such that current is induced in the wire coil when the external wire coil is positioned adjacent to the wire coil.

In embodiments the rolling bladder is positioned between a first vertebrae and a second vertebrae such that expansion of the rolling bladder changes a spacing between the first vertebrae and second vertebrae.

In embodiments, the system includes another rolling bladder in fluid communication with the pump and configured to expand into the expanded state and retract into the retracted state.

In embodiments, the first pump includes: a first bellows including eutectic wax; and a first heating element electrically connected to the power source, wherein the first heating element is positioned such that when power is provided to the first heating element, the eutectic wax melts and the first bellows expands and when power is removed from the first heating element, the eutectic wax cools and solidifies and the first bellows retracts.

In embodiments, the second pump includes: a second bellows including eutectic wax; and a second heating element electrically connected to the power source, wherein the second heating element is positioned such that when power is provided to the second heating element, the eutectic wax melts and the second bellows expands and when power is removed from the second heating element, the eutectic wax cools and solidifies and the second bellows retracts.

A spinal adjustment system in accordance with an embodiment of the present disclosure includes: a first rolling bladder configured expand from a retracted state to an extended state and from the extended state to the retracted state; a second rolling bladder configured to expand from a retracted state to an extended state and from the extended state to the retracted state; and a pump in fluid communication with the first rolling bladder and the second rolling bladder and configured to provide a working fluid to the first rolling bladder and the second rolling bladder such that the first rolling bladder and the second rolling bladder, respectively, extend to the extended state, and to remove working fluid from the first rolling bladder and the second rolling bladder such that the first rolling bladder and the second rolling bladder, respectively, retract to the retracted state, the pump including: a first volume filled with the working fluid; a first pump element mounted in the first volume and operable to expand when activated to pump the working fluid out of the first volume; a second volume filled with the working fluid; a second pump element mounted in the second volume and operable to expand when activated to pump the working fluid out of the second volume; wherein the first rolling bladder and second rolling bladder are in fluid communication with the first volume and the second volume and expand to the expanded state when working fluid flows into the first rolling bladder and the second rolling bladder to retract when the working fluid flows out of the first rolling bladder and the second rolling bladder; an accumulator in fluid communication with the first volume and the second volume; a power source electrically connected the first pump and the second pump, and operable to selectively provide power to the first pump and the second pump; wherein, the first pump element expands when power is provided to the first pump element to increase pressure in the first volume to pump the working fluid from the first volume into the first rolling bladder and the second rolling bladder such that the first rolling bladder and the second rolling bladder expand to the extended state; and wherein, the second pump element expands when power is provided to the second pump element to increase pressure in the second volume to pump working fluid from the second volume into the accumulator and retracts when power is removed from the second pump element such that fluid drains from the first rolling bladder and the second rolling bladder into the second volume and the first rolling bladder and the second rolling bladder retract to the retracted state.

In embodiments, the system includes: a first check valve positioned between the first volume and the first rolling bladder and the second rolling bladder and configured to control flow of working fluid from the first volume to the first rolling bladder and the second rolling bladder; a second check valve positioned between the first volume and the accumulator and configured to control flow of working fluid between first volume and the accumulator; a third check valve positioned between the second volume and the first rolling bladder and the second rolling bladder and configured to control flow of working fluid from the first rolling bladder and the second rolling bladder to the second volume; and a relief valve position between the second volume and the accumulator and configured to control flow of working fluid from the second volume to the accumulator.

In embodiments the first check valve allows working fluid to flow from the first volume to the first rolling bladder and the second rolling bladder when the first pump element expands and prevents working fluid from flowing back into the first volume when the first pump retracts after power is removed.

In embodiments, the second check valve allows working fluid to flow from the accumulator into the first volume when the first pump element retracts after power is removed.

In embodiments, the relief valve is configured to allow working fluid to flow from the second volume to the accumulator when the second pump element expands when power is applied to the second pump element.

In embodiments, the third check valve is configured to allow the working fluid to flow from the first rolling bladder and the second rolling bladder to the second volume such that the first rolling bladder and the second rolling bladder return to the retracted state when the second pump retracts after power is removed.

In embodiments, the power supply is a wire coil.

In embodiments, the system includes power supply circuitry configured to selectively provide power to one of the first pump element and the second pump element.

In embodiments, the power supply circuitry includes: a first diode positioned between the wire coil and the first pump element such that power is provided to the first power pump when current is induced in the wire coil using a rectified sinusoidal signal having a first polarity; and a second diode positioned between the wire coil and the second pump element such that power is provided to the second power pump when current is induced in the wire coil using a rectified sinusoidal signal having a second polarity, opposite the first polarity.

A spinal adjustment system in accordance with an embodiment of the present disclosure includes: a first rolling bladder configured expand from a retracted state to an extended state and from the extended state to the retracted state; a first pump in fluid communication with the first rolling bladder and configured to provide a working fluid to the first rolling bladder such that the first rolling bladder extends to the extended state and to remove working fluid from the first rolling bladder such that the first rolling bladder retracts to the retracted state, the first pump including: a first volume filled with the working fluid; a first pump element mounted in the first volume and operable to expand when activated to pump the working fluid out of the first volume; a second volume filled with the working fluid; a second pump element mounted in the second volume and operable to expand when activated to pump the working fluid out of the second volume; wherein the first rolling bladder is in fluid communication with the first volume and the second volume and expand to the expanded state when working fluid flows into the first rolling bladder to retract when the working fluid flows out of the first rolling bladder; an accumulator in fluid communication with the first volume and the second volume; a power source electrically connected the first pump element and the second pump element, and operable to selectively provide power to the first pump element and the second pump element; wherein, the first pump element expands when power is provided to the first pump element to increase pressure in the first volume to pump the working fluid from the first volume into the first rolling bladder such that the first rolling bladder expands to the extended state; and wherein, the second pump element expands when power is provided to the second pump element to increase pressure in the second volume to pump working fluid from the second volume into the accumulator and retracts when power is removed from the second pump element such that fluid drains from the first rolling bladder into the second volume and the first rolling bladder retracts to the retracted state; and a second rolling bladder configured expand from a retracted state to an extended state and from the extended state to the retracted state; a second pump in fluid communication with the second rolling bladder and configured to provide a working fluid to the second rolling bladder such that the first rolling bladder extends to the extended state and to remove working fluid from the second rolling bladder such that the second rolling bladder retracts to the retracted state, the second pump including: a third volume filled with the working fluid; a third pump element mounted in the third volume and operable to expand when activated to pump the working fluid out of the third volume; a fourth volume filled with the working fluid; a fourth pump element mounted in the fourth volume and operable to expand when activated to pump the working fluid out of the fourth volume; wherein the second rolling bladder is in fluid communication with the third volume and the fourth volume and expand to the expanded state when working fluid flows into the second rolling bladder to retract when the working fluid flows out of the second rolling bladder; a second accumulator in fluid communication with the third volume and the fourth volume; a second power source electrically connected the third pump element and the fourth pump element, and operable to selectively provide power to the third pump element and the fourth pump element; wherein, the third pump element expands when power is provided to the third pump element to increase pressure in the third volume to pump the working fluid from the third volume into the second rolling bladder such that the second rolling bladder expands to the extended state; and wherein, the fourth pump element expands when power is provided to the fourth pump element to increase pressure in the fourth volume to pump working fluid from the fourth volume into the second accumulator and retracts when power is removed from the fourth pump element such that fluid drains from the second rolling bladder into the fourth volume and the second rolling bladder retracts to the retracted state.

BRIEF DESCRIPTION OF THE DRAWINGS

The above and related objects, features and advantages of the present disclosure will be more fully understood by reference to the following detailed description of the preferred, albeit illustrative, embodiments of the present invention when taken in conjunction with the accompanying figures, wherein:

FIG. 5A illustrates a spinal alignment system including a plurality of rolling bladders in an extended position in accordance with an embodiment of the present application;

FIG. 5B illustrates the spinal alignment system of FIG. 1 including a plurality of rolling bladders in a retracted position in accordance with an embodiment of the present application;

FIG. 6 illustrates an exemplary embodiment of a pump suitable for use in the spinal alignment system of FIG. 1 mounted in an exemplary housing in accordance with an embodiment of the present application;

FIG. 8 illustrates an exemplary cross-sectional view of the pump mechanism of FIGS. 7A-7C along line A-A in accordance with an embodiment of the present disclosure;

DETAILED DESCRIPTION OF THE EXEMPLARY EMBODIMENTS

Figure 1:
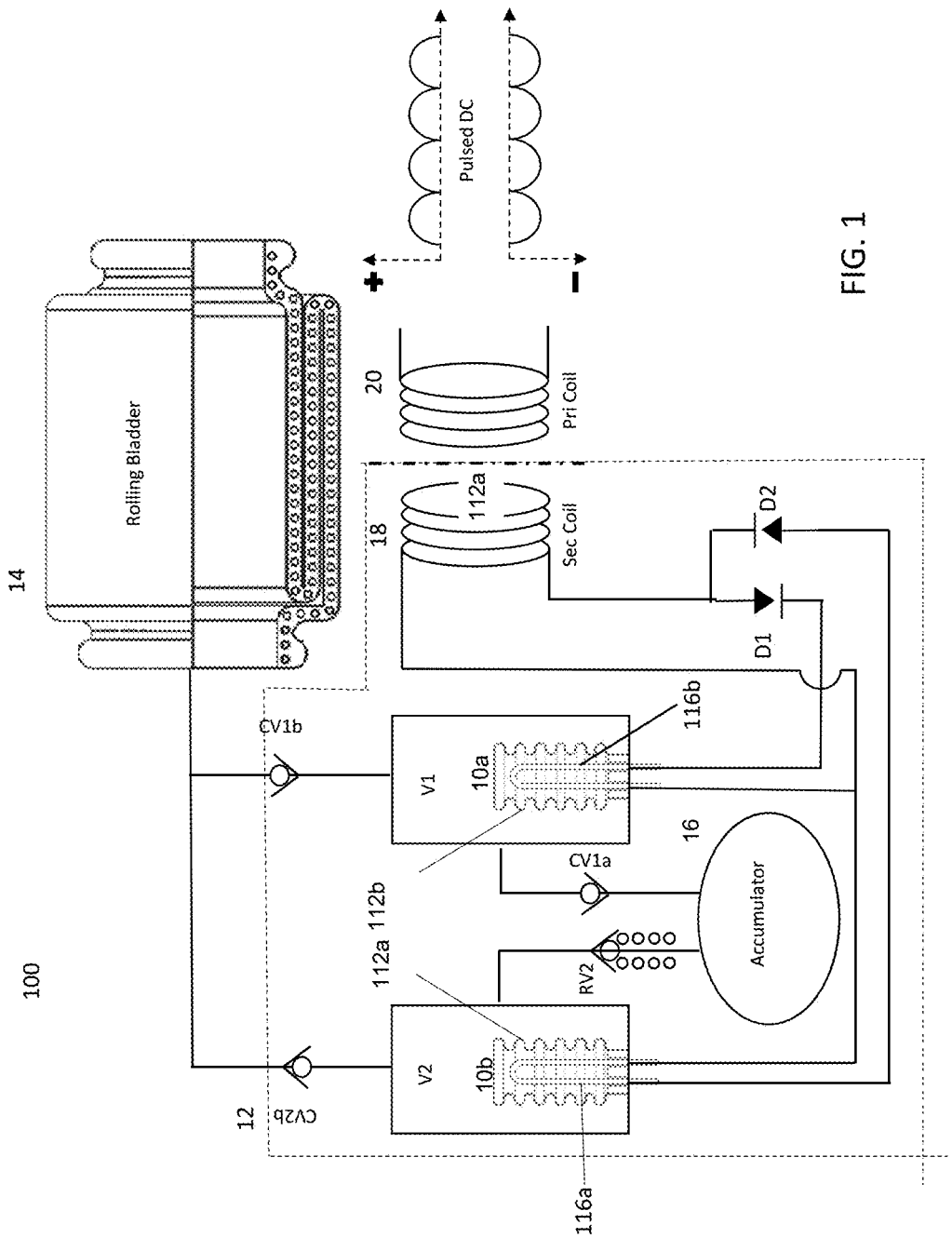
FIG. 1 illustrates an exemplary block diagram of a spinal alignment system in accordance with an embodiment of the present application.

FIG. 1 illustrates an exemplary block diagram of a spinal alignment system 100 that may include a pump mechanism 12 connected to a rolling bladder 14. In embodiments, the pump mechanism 12 may include a pair of thermally actuated pumps (cartridges) 10a, 10b that function to either pump fluid from the accumulator 16 to the rolling bladder 14 or from the rolling bladder to the accumulator 16. In embodiments, the accumulator 16 may be a zero-pressure reference fluid reservoir that stores working fluid for the system 100. In one such embodiment, the accumulator 16 may be connected to the pump mechanism 12 with a catheter and implanted along with the fluid pump as opposed to being integral with the fluid pump. In embodiments, the accumulator 16 may be or may include an expandable bag made of polyvinyl chloride (PVC) much like that of an IV bag used externally. In embodiments, the expandable bag may be constructed of a selectively permeable membrane allowing for the water, which may be used as the working fluid, within the body to replenish the fluid supply within the accumulator 16. In embodiments, the rolling bladder 14 may be a type of hydraulic element that when pressurized with the working fluid provides a expansive force and accompanying expansion depending on the design requirements.

In embodiments, electric power to the pump mechanism 12, and specifically the thermally actuated pumps 10a, 10b may be provided by a power source 18. In embodiments, the power source 18 may be an inductively coupled coil as can be seen in FIG. 1, for example. In embodiments, the power source 18 may be a multi-turn induct coil and may be positioned in a patient's body just under the patient's skin. In embodiments, a plane of the coil is substantially parallel to the surface of the patient's skin to facilitate efficient coupling with an external primary coil 20. In embodiments, the power source 18 may be an onboard power source, such as a battery, for example. In embodiments, the power source 18 (coil) may be part of a near field charging system that requires no actual physical connection to the exterior of the patient to provide power. In embodiments, an external primary coil 20 may be energized with a rectified sinusoidal current of a positive or negative polarity. In embodiments, the rectified sinusoidal current may be used to induce a current in the secondary coil 18 which may be directed to a heating element 116a or 116b of the two thermally actuated pumps 10a, 10b via the diodes D1, D2. In embodiments, other suitable power supply circuitry may be used in place of the diodes D1, D2 to selectively provide power to and activate the first pump 10a and the second pump 10b. In embodiments, the power supply circuitry may include a processor or other control circuit. In embodiments, the power supply circuitry may be used to manage power consumption, for example, where the power source 18 includes a battery, for example.

Figure 4C:
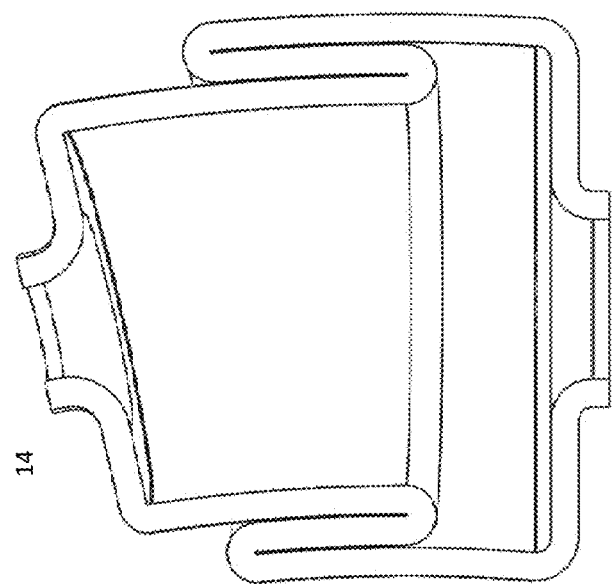
FIG. 4C illustrates an exemplary rolling bladder used in the spinal alignment system of FIGS. 1-3 in a partially extended position depicting the bladders ability expand along a curved trajectory in accordance with an embodiment of the present application.
Figure 4B:
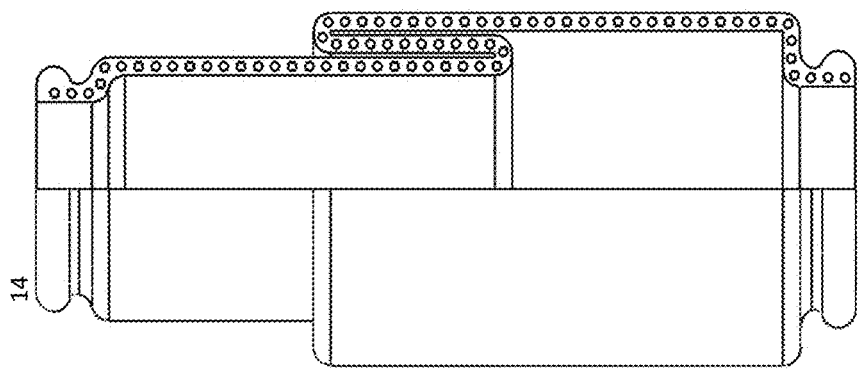
FIG. 4B illustrates an exemplary rolling bladder used in the spinal alignment system of FIGS. 1-3 in an extended position in accordance with an embodiment of the present application.

In embodiments, in order to control expansion of the rolling bladder 14, the pulsed current of a positive rectified sinusoidal signal in the primary coil 20 induces a secondary current in the coil 18 that is provided to the thermally actuated pump 10a positioned in the working fluid filled volume V1 causing it to expand and increase the pressure in the volume V1 and forcing the trapped working fluid through check valve CV1b while checking valve CV1a. In embodiments, the working fluid may flow into the rolling bladder 14 causing it to expand to an expanded state, as can be seen in FIG. 4B. In embodiments, although pressure is communicated across check valve CV2b into the volume V2, the ridged nature of the thermally actuated pump 10b in the volume V2 and the pressure relief valve RV2 prevent any fluid from returning to the accumulator 16. When the thermally actuated pump 10a is deactivated, it retracts and the reduced pressure draws working fluid from the accumulator 16 through check valve CV1a while the checked state of CV1b retains the pressure within the rolling bladder 14 to maintain the extended position of the bladder 14.

Figure 4A:
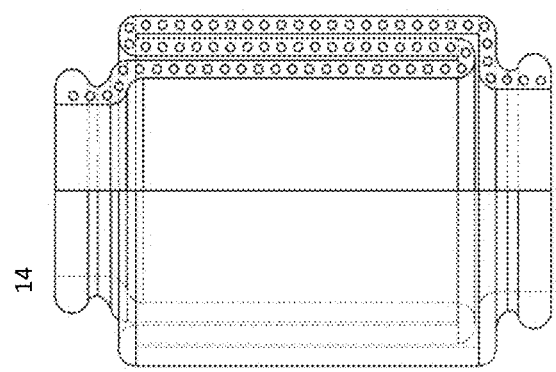
FIG. 4A illustrates an exemplary rolling bladder used in the spinal alignment system of FIGS. 1-3 in a retracted position in accordance with an embodiment of the present application.

In embodiments, in order to retract the rolling bladder 14 to a retracted state, as illustrated in FIG. 4A, for example, the pulsed current in the primary coil 20 may be reversed, for example, by providing a rectified sinusoidal signal of opposite polarity, which routes secondary current via the coil 18 to the thermally actuated pump 10b in the volume V2. As the thermally actuated pump 10b in V2 expands, check valve CV2b is checked (closed) and pressure builds up within volume V2 until the relief valve RV2 relieves the pressure sending fluid from volume V2 to the accumulator 16. Once current is removed, the thermally actuated pump 10b retracts, lowering the pressure in volume V2 causing the relief value RV2 to close. Further contraction of the thermally actuated pump 10b in volume V2 reduces the pressure in V2 further until check valve CV2b opens allowing fluid to flow from the rolling bladder 14 back into volume V2. The removal of working fluid from the rolling bladder 14 causes the pressure within it to drop resulting in a contraction of the bladder 14 to the retracted state. In embodiments, the thermally actuated pumps 10a, 10b may include respective bellows structures 112a, 112b (see FIG. 1, for example) holding a thermally responsive material, such as a eutectic wax, and respective heating elements 116a, 116b that when activated, heat the wax such that it melts and expands to expand the bellows structures 116a, 116b. When the heating elements 116a, 116b are deactivated, the wax cools, solidifies and contracts such that the bellows structures 112a, 112b retract. In embodiments, the bellows structures 112a, 112b may be biased into the retracted position. In embodiments, the first thermally actuated pump 10a and the second thermally actuated pump 10b may be embodied by the thermally actuated actuator component described in Applicant's co-pending U.S. Nonprovisional patent application Ser. No. 17/176,732, filed Feb. 16, 2021 entitled BIDIRECTIONAL THERMALLY ACTUATED COMPONENT FOR USE IN MEDICAL DEVICES, the entire content of which is incorporated herein by reference. In embodiments, the power source 18 may be electrically connected to the respective heating elements 116a, 116b that are used to apply heat to the expandible bellows structures 112a, 112b and the eutectic wax included therein.

Figure 2:
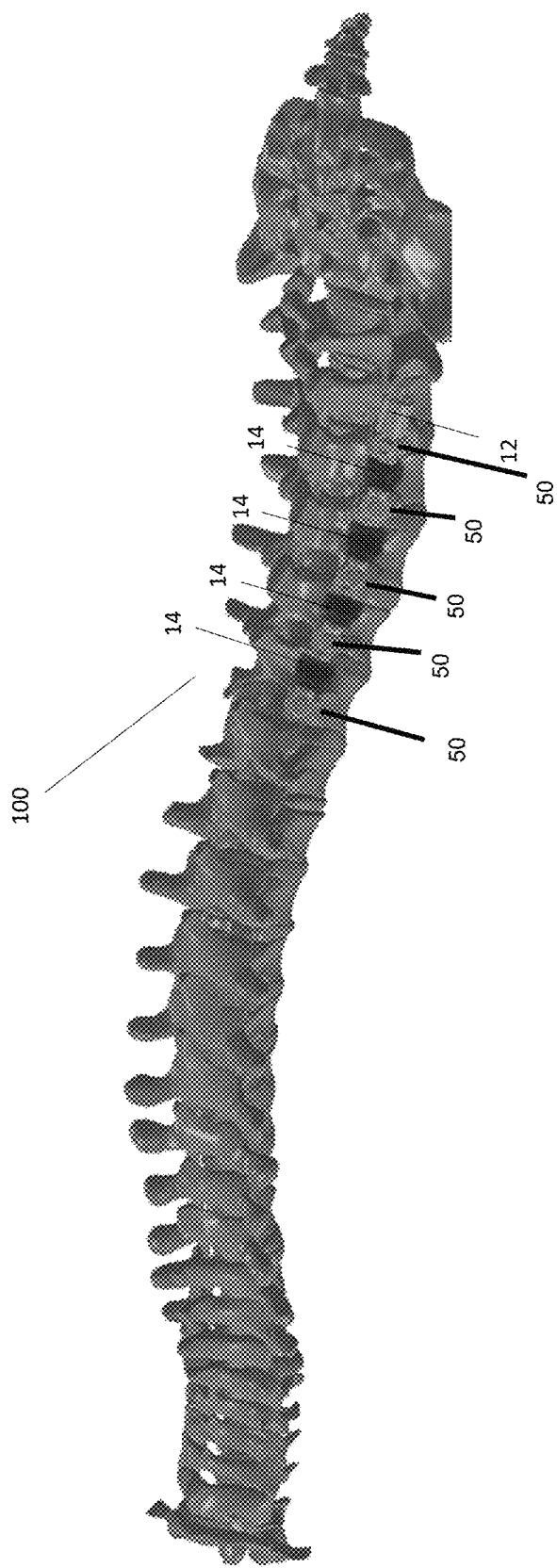
FIG. 2 illustrates an exemplary schematic representation of the spinal alignment system provided on multiple vertebrae on a user's spine in accordance with an embodiment of the present application.
Figure 3:
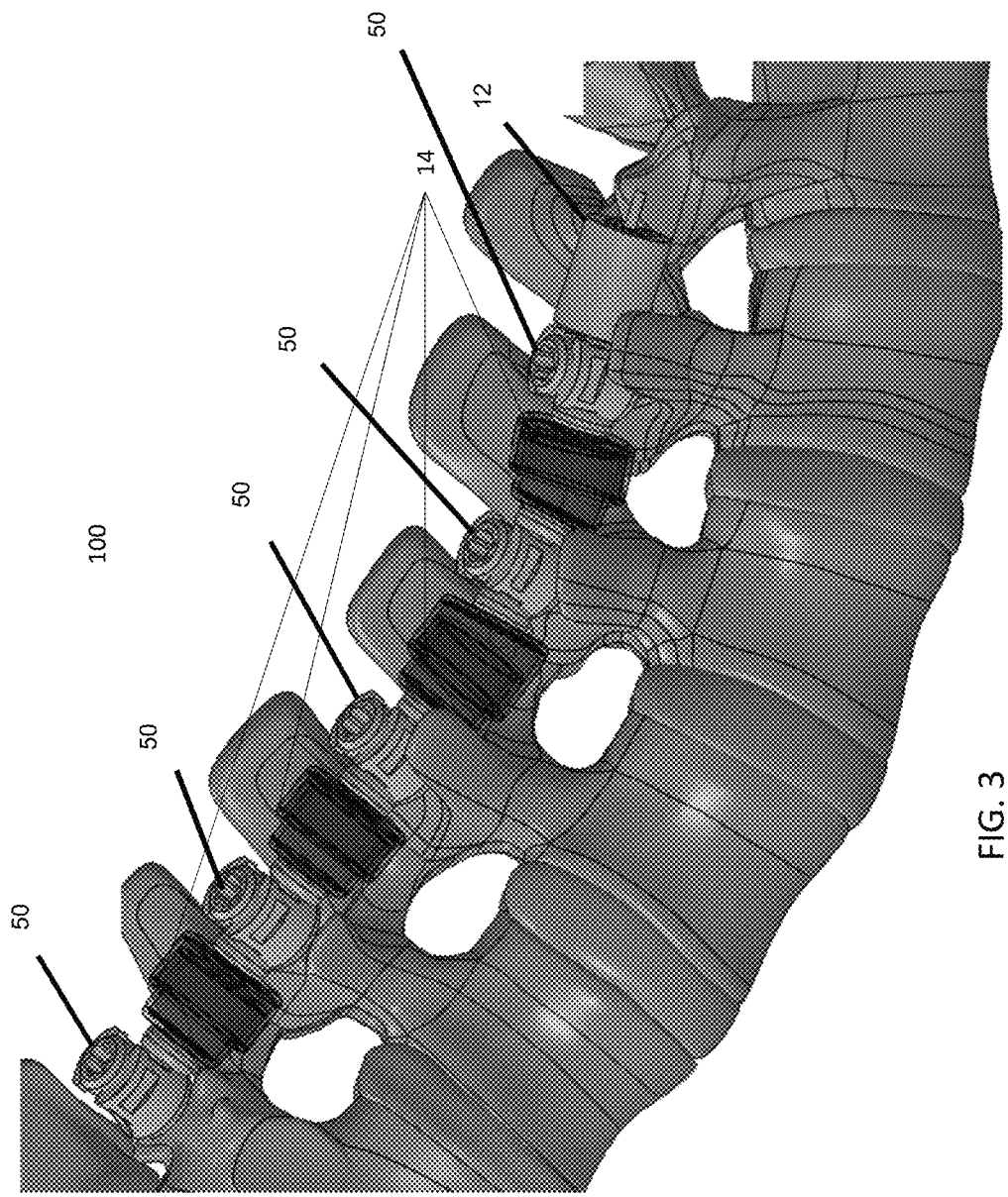
FIG. 3 illustrates a more detailed view of the exemplary schematic representation of FIG. 2 in accordance with an embodiment of the present application.

In embodiments, the rolling bladder 14 may be used to apply force to one or more vertebrae in a user's spine. In embodiments, the rolling bladder 14 may be controlled to expand and contract as desired to provide pressure to encourage alignment of the vertebrae. In embodiments, multiple bladders 14 may be used to apply pressure to multiple vertebrae, as can be seen in FIGS. 2-3, for example. In embodiments, the bladders 14 may be individually controlled to apply different amounts of pressure to different vertebrae. In embodiments, fasteners 50 may be secured to the vertebrae and the rolling bladders 14 may be positioned between the fasteners. In embodiments, the fasteners 50 may be pedicle screws, as illustrated in FIG. 5B, for example. In embodiments, a respective pump mechanism 12 may be connected through element 40 and may be used to control expansion and retraction of a respective rolling bladder 14 to adjust spacing between the vertebrae that the fasteners 50 are attached to. In embodiments, each of the respective pump mechanisms 12 may be separately controlled such that each rolling bladder 14 may be individually controlled to provide desired spacing between specific pairs of vertebrae. In embodiments, each of the respective pump mechanisms 12 may be separately controlled by separately controlling power to each of the respective pumps 12.

In embodiments, the rolling bladders 14 may be controlled together. In embodiments, a single pump 12 may be provided in fluid communication with each of the rolling bladders 14. In embodiments, the single pump mechanism 12 may be mounted in a housing 110, as illustrated in FIG. 6, for example. In embodiments, the single pump mechanism 12 may be operable to provide working fluid to each of the rolling bladders 14 illustrated in FIGS. 2-3, for example. In embodiments, the fasteners 50 may include fluid connectors (item 40a) to allow for the flow of working fluid from the pump mechanism 12 to the multiple rolling bladders 14 in FIG. 3, for example. In embodiments, an end connector 40b may be provided at an end of the system 100.

FIG. 4A illustrates an exemplary embodiment of a rolling bladder 14 in a retracted state or position. FIG. 4B illustrates an exemplary embodiment of a rolling bladder 14 in an extended state or position. FIG. 4C illustrates a cross-sectional view of a rolling bladder 14 in a partially extended position. In embodiments, the rolling bladder 14 may include flexible walls and may be biased into the retracted position illustrated in FIG. 4A. In embodiments, as working fluid flows into the rolling bladder 14, pressure in the rolling bladder 14 increases such that the flexible walls expand into the extended state. When working fluid is drained from the rolling bladder 14, the pressure in the bladder falls and the flexible walls retract into the retracted state.

FIG. 5A illustrates an example of a spinal alignment system 100 including several rolling bladders 14 connected together in an extended position. FIG. 5B illustrates an example of a spinal alignment system 100 including several rolling bladders 14 connected together in a retracted position. In embodiments, the rolling bladders 14 are connected via connecting elements 40. In embodiments, the connecting elements 40 include fluid conduits 40a extending therethrough providing fluid communication between the rolling bladders 14 such that the rolling bladders expand and retract together. In embodiments, the connecting elements 40 may be, or may include the fasteners 50 which are connected to the vertebrae and the rolling bladder 14 maybe provide between them. In embodiments, the spinal alignment system 100 may include a pump connector 60 provided at one end of the system 100 and configured to provide a fluid connection between the pump 12 discussed above and the rolling bladders 14 to provide working fluid to the rolling bladders and allow it to be drained therefrom. In embodiments, the pump connector 60 may include a working fluid inlet 60a in fluid communication with the pump mechanism 12 and the rolling bladders 14. In embodiments, the rolling bladders 14 may be connected to individual pump mechanisms 12 in which case the passages 40a in the connecting elements 40 may be elbow shaped and connected to respective pump mechanisms.

Figure 7C:
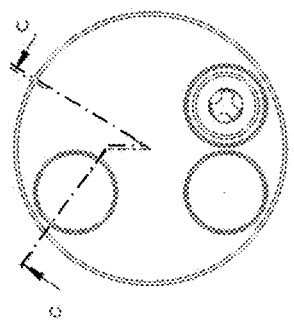
FIG. 7C illustrates an exemplary opposite end view of the pump mechanism of FIG. 7A in accordance with an embodiment of the present disclosure.
Figure 7D:
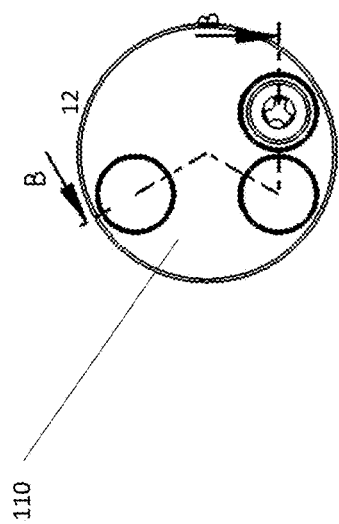
FIG. 7D illustrates another exemplary opposite end view of the pump mechanism of FIG. 7A in accordance with an embodiment of the present disclosure.
Figure 7A:
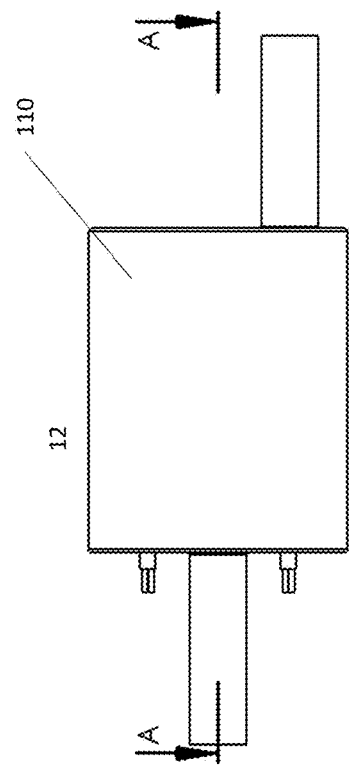
FIG. 7A illustrates an exemplary side view of a pump mechanism mounted in a housing in accordance with an embodiment of the present disclosure.
Figure 7B:
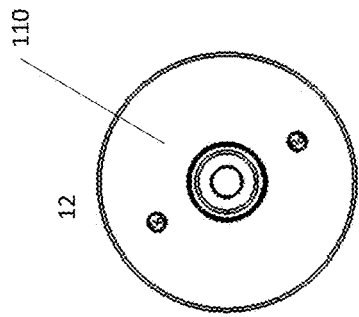
FIG. 7B illustrates an exemplary end view of the pump mechanism of FIG. 7A in accordance with an embodiment of the present disclosure.
Figure 9:
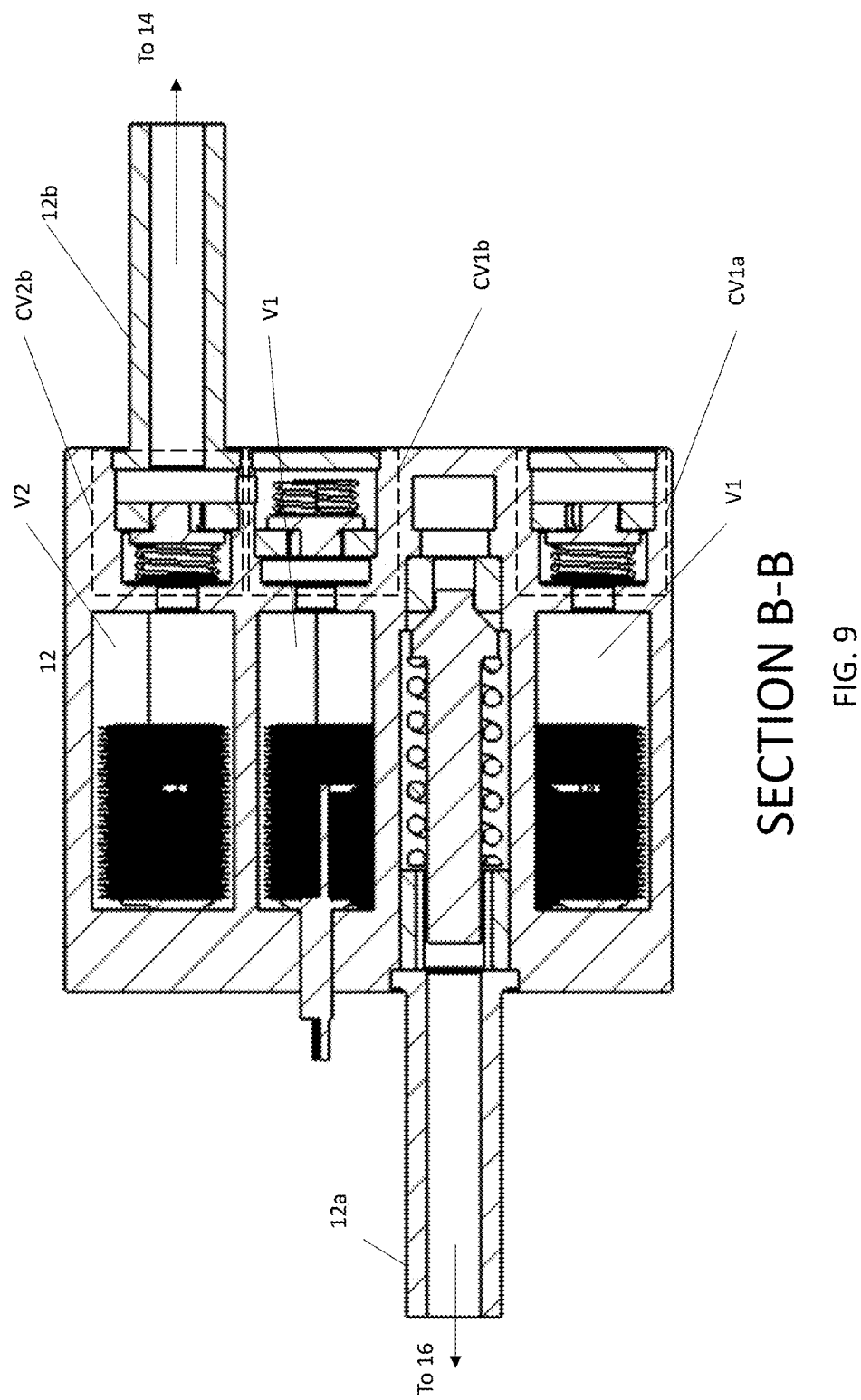
FIG. 9 illustrates an exemplary cross-sectional view of the pump mechanism of FIGS. 7A-7C along line B-B in accordance with an embodiment of the present disclosure.

FIG. 6 illustrates an exemplary schematic view of the pump mechanism 12 mounted in a housing 110 for use in the system 100 in FIGS. 1-3 and 5A. In embodiments, volume V1 and volume V2 may be integrated as separate compartments in the housing 110. In embodiments, the pump 10a, including bellows 112a, may be mounted in the volume V1 and the pump 10b, including bellows 112b, may be mounted in the volume V2. In embodiments, the accumulator 16 may be provided outside of the housing 110 and may be connected to the pumps 10a, 10b via a catheter, for example, as noted above. FIG. 7A illustrates a side view of the pump mechanism 12 mounted in the housing illustrated in FIG. 6 along with a section line A-A the details of which are shown in FIG. 8. FIG. 7B illustrates an end view thereof and FIG. 7C illustrates the opposite end view along with section line B-B the details of which are shown in FIG. 9. FIG. 7D shows the section line C-C the details of which are shown in FIG. 10.

FIG. 8 illustrates an exemplary cross-sectional view of the pump mechanism 12 of FIG. 7A along line A-A. FIG. 8 illustrates tube stub, or connector, 12a providing fluid communication with the accumulator 16 positioned outside of the housing 110 such that working fluid may flow between the pump mechanism and the accumulator. The tube stub, or connector, 12b provides fluid communication with the rolling bladder(s) 14 such that fluid may flow between the pump mechanism and the rolling bladder(s) 14. FIG. 8 also shows the cross-section of the first pump 10a, and the second pump 10b, which may be thermal wax expansion elements, positioned within volumes V1 and V2. The relief valve RV2 of FIG. 8 is shown in detail in FIG. 11.

FIG. 9 illustrates a cross-sectional view of the pump mechanism 12 of FIG. 7C along the line B-B. FIG. 9 also shows exemplary placement of each of the check valves CV1a, CV1b, and CV2b which are shown in detail in FIG. 12.

Figure 10:
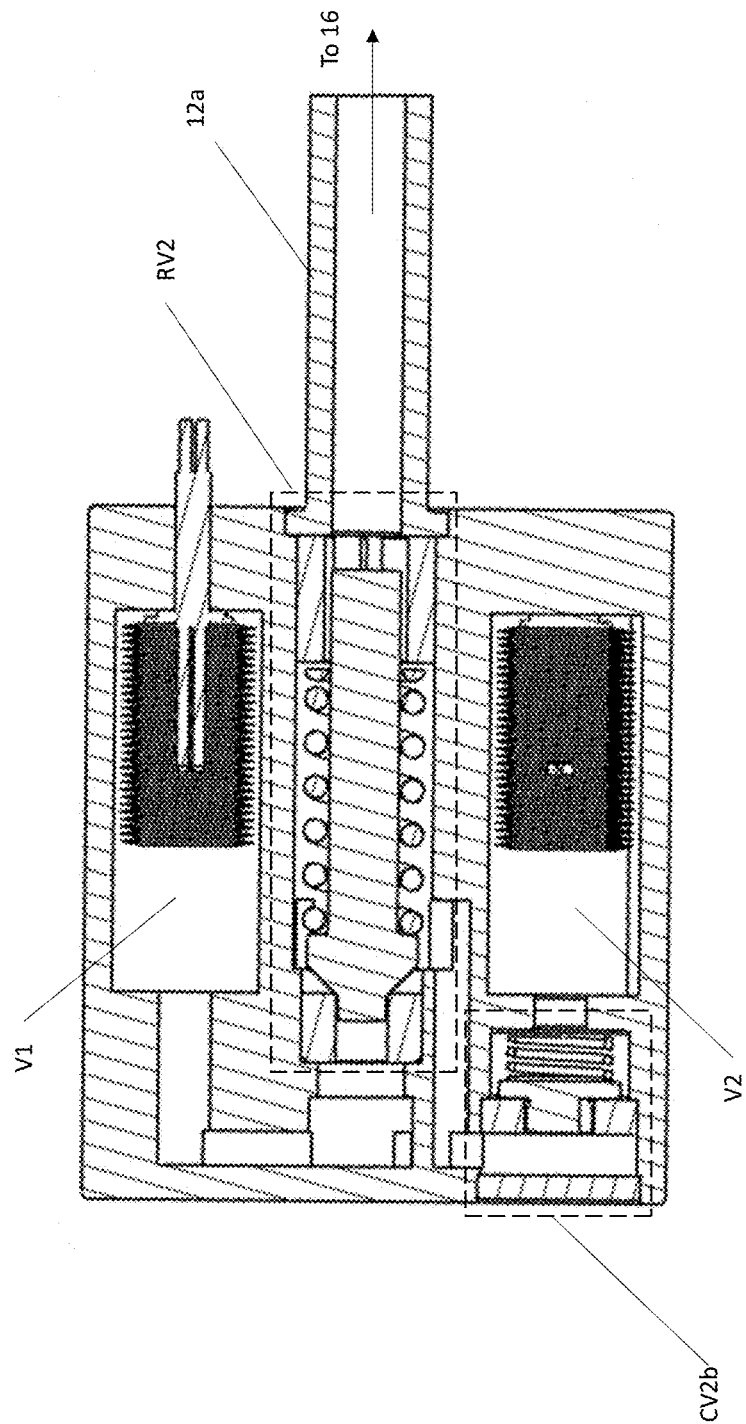
FIG. 10 illustrates an exemplary cross-sectional view of the pump mechanism of FIGS. 7A-7D along the line C-C in accordance with an embodiment of the present disclosure.

FIG. 10 illustrates a cross-sectional view of the pump mechanism 12 of FIG. 7D along the line C-C illustrating exemplary fluid passage connections between V1, RV2 and V2, CV2b and RV2 and their connection to the accumulator 16.

Figure 11:
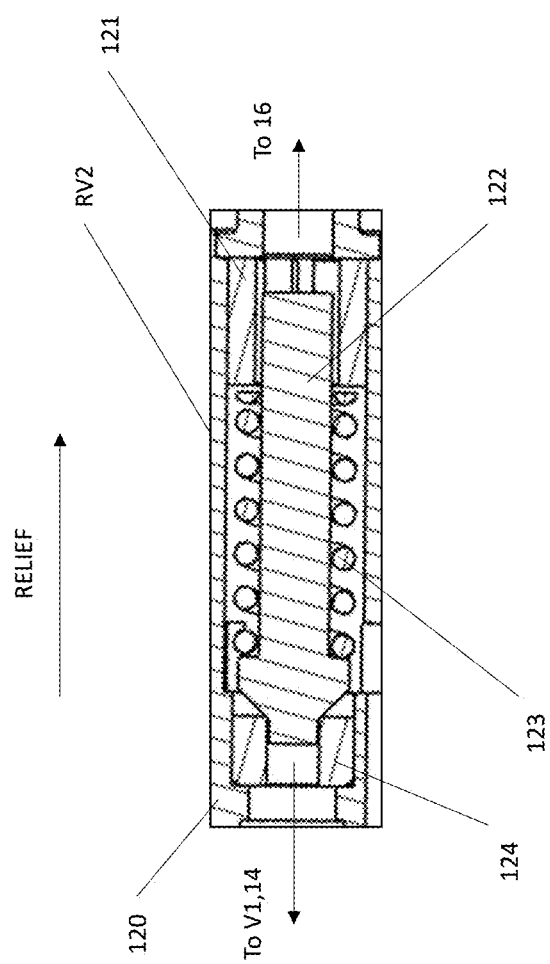
FIG. 11 illustrates an exemplary cross-sectional view of an exemplary relief valve used in the pump mechanism of FIGS. 7A-7D in accordance with an embodiment of the present disclosure.

FIG. 11 shows a cross sectional view of the relief valve RV2. In embodiments, as illustrated, the relief valve RV2 may be a direct acting spring loaded poppet type relief valve. In embodiments, the relief valve RV2 may include a housing 120, a seat 124, a poppet 122 which is guided within guide 121 and/or seat 124 and preloaded with spring 123. The preload of the spring 123 acting on the poppet 122 forces the poppet 122 against the seat 124 affecting a seal against fluid pressure in volume V1 and rolling bladder 14. If the pressure in V1, 14 acting on the area of the seat diameter develops a force equal or greater than the spring 123 force, the relief valve RV2 will open and allow fluid to flow from V1,14 to accumulator 16. The pressure threshold desired is a function of the desired force in the rolling bladder 14 and the cross-sectional area of the same and will be dependent on patient specifics. Other relief valve configurations may be used as appropriate based on the packing and performance parameters desired.

Figure 12:
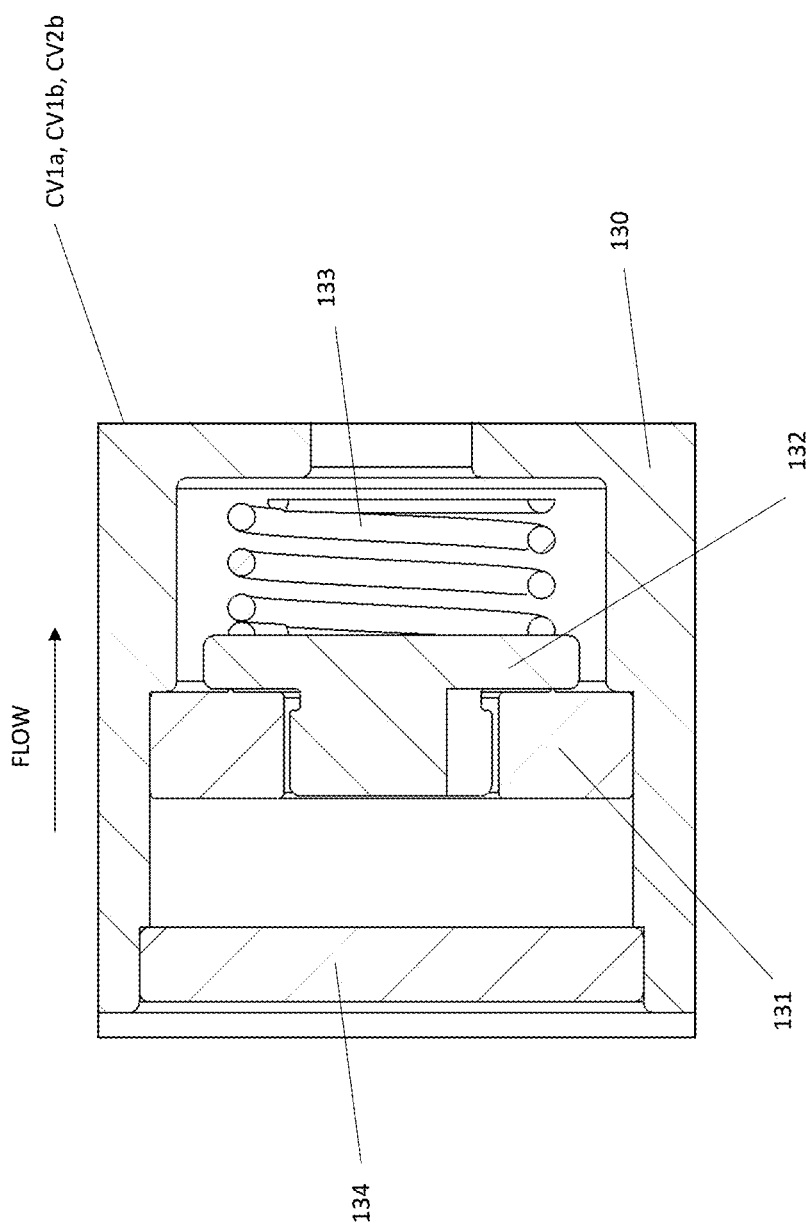
FIG. 12 illustrates an exemplary cross-sectional view of an exemplary check valve used in the pump mechanism of FIGS. 7A-7D in accordance with an embodiment of the present disclosure.

FIG. 12 illustrates a cross-sectional view of exemplary check valves CV1a, CV1b, CV2b. Similar to the relief valve RV2, the check valves of FIG. 12 are illustrated as a direct acting, spring loaded, poppet type check valve. In embodiments, each check valve may include a housing 130, a seat 131, a poppet 132 which is guided within the seat 131 and preloaded with spring 133. An endcap 134 may be included to facilitate assembly in the housing. In embodiments, the check valves CV1a, CV1b, CV2b use a small spring force to bias the poppet 132 closed. Pressure acting in the check direction, opposite of the flow direction, further enhances the force acting to close the check valve preventing flow in the checked direction. These check valves CV1a, CV1b, CV2b act to control the flow of working fluid as described with reference to FIG. 1.

In embodiments, the power source 18 may be mounted under a user's skin and the primary coil 20 may be provided externally to induce the current in pump mechanism 12.

Now that embodiments of the present invention have been shown and described in detail, various modifications and improvements thereon can become readily apparent to those skilled in the art. Accordingly, the exemplary embodiments of the present invention, as set forth above, are intended to be illustrative, not limiting. The spirit and scope of the present invention is to be construed broadly.

What is claimed is:

1. A spinal adjustment system comprising:
    a rolling bladder configured to expand from a retracted state to an extended state and from the extended state back to the retracted state; and
    a pump connected to the rolling bladder and configured to provide a working fluid to the rolling bladder such that the rolling bladder extends to the extended state and to remove working fluid from the rolling bladder such that the rolling bladder retracts to the retracted state,
    the pump including:
        a first volume filled with the working fluid;
        a first pump element mounted in the first volume and operable to expand when activated to pump the working fluid out of the first volume;
        a second volume filled with the working fluid;
        a second pump element mounted in the second volume and operable to expand when activated to pump the working fluid out of the second volume;
        wherein the rolling bladder is in fluid communication with the first volume and the second volume and expands to the expanded state when working fluid flows into the rolling bladder and to retract when the working fluid flows out of the rolling bladder;
        an accumulator in fluid communication with the first volume and the second volume;
        a power source electrically connected to the first pump element and the second pump element, and operable to selectively provide power to the first pump and the second pump;
        wherein, the first pump element expands when power is provided to the first pump element to increase pressure in the first volume to pump the working fluid from the first volume into the rolling bladder such that the rolling bladder expands to the extended state; and
        wherein, the second pump element expands when power is provided to the second pump element to increase pressure in the second volume to pump working fluid from the second volume into the accumulator and retracts when power is removed from the second pump element such that fluid drains from the rolling bladder into the second volume and the rolling bladder retracts to the retracted state.

2. The system of claim 1, further comprising:
    a first check valve positioned between the first volume and the rolling bladder and configured to control flow of working fluid from the first volume to the rolling bladder;
    a second check valve positioned between the first volume and the accumulator and configured to control flow of working fluid between first volume and the accumulator;
    a third check valve positioned between the second volume and the rolling bladder and configured to control flow of working fluid from the rolling bladder to the second volume; and
    a relief valve position between the second volume and the accumulator and configured to control flow of working fluid from the second volume to the accumulator.

3. The system of claim 2, wherein the first check valve allows working fluid to flow from the first volume to the rolling bladder when the first pump element expands and prevents working fluid from flowing back into the first volume when the first pump element retracts after power is removed.

4. The system of claim 2, wherein the second check valve allows working fluid to flow from the accumulator into the first volume when the first pump element retracts after power is removed.

5. The system of claim 2, wherein the relief valve is configured to allow working fluid to flow from the second volume to the accumulator when the second pump element expands when power is applied to the second pump element.

6. The system of claim 2, wherein the third check valve is configured to allow the working fluid to flow from the rolling bladder to the second volume such that the rolling bladder returns to the retracted state when the second pump element retracts after power is removed.

7. The system of claim 1, wherein the power source is a wire coil.

8. The system of claim 7, further comprising power source circuitry configured to selectively provide power to one of the first pump element and the second pump element.

9. The system of claim 8, wherein the power source circuitry comprises:
    a first diode positioned between the wire coil and the first pump element such that power is provided to the first pump element when current is induced in the wire coil using a rectified sinusoidal signal having a first polarity; and
    a second diode positioned between the wire coil and the second pump element such that power is provided to the second pump element when current is induced in the wire coil using a rectified sinusoidal signal having a second polarity, opposite the first polarity.

10. The system of claim 7, wherein the wire coil is paired with an external wire coil such that current is induced in the wire coil when the external wire coil is positioned adjacent to the wire coil.

11. The system of claim 1, wherein the rolling bladder is positioned between a first vertebrae and a second vertebrae such that expansion of the rolling bladder changes a spacing between the first vertebrae and second vertebrae.

12. The system of claim 1, further comprising another rolling bladder in fluid communication with the the first volume and the second volume and configured to expand into the expanded state and retract into the retracted state.

13. The system of claim 1, wherein the first pump element comprises:
    a first bellows including eutectic wax; and
    a first heating element electrically connected to the power source;
    wherein the first heating element is positioned such that when power is provided to the first heating element, the eutectic wax melts and the first bellows expands and when power is removed from the first heating element, the eutectic wax cools and solidifies and the first bellows retracts.

14. The system of claim 13, wherein the second pump element comprises:
    a second bellows including eutectic wax; and
    a second heating element electrically connected to the power source;

wherein the second heating element is positioned such that when power is provided to the second heating element, the eutectic wax melts and the second bellows expands and when power is removed from the second heating element, the eutectic wax cools and solidifies and the second bellows retracts.

15. A spinal adjustment system comprising:
a first rolling bladder configured to expand from a retracted state to an extended state and from the extended state to the retracted state;
a second rolling bladder configured to expand from a retracted state to an extended state and from the extended state to the retracted state; and
a pump in fluid communication with the first rolling bladder and the second rolling bladder and configured to provide a working fluid to the first rolling bladder and the second rolling bladder such that the first rolling bladder and the second rolling bladder, respectively, extend to the extended state, and to remove working fluid from the first rolling bladder and the second rolling bladder such that the first rolling bladder and the second rolling bladder, respectively, retract to the retracted state,
the pump including:
    a first volume filled with the working fluid;
    a first pump element mounted in the first volume and operable to expand when activated to pump the working fluid out of the first volume;
    a second volume filled with the working fluid;
    a second pump element mounted in the second volume and operable to expand when activated to pump the working fluid out of the second volume;
    wherein the first rolling bladder and second rolling bladder are in fluid communication with the first volume and the second volume and expand to the expanded state when working fluid flows into the first rolling bladder and the second rolling bladder and retract when the working fluid flows out of the first rolling bladder and the second rolling bladder;
    an accumulator in fluid communication with the first volume and the second volume;
    a power source electrically connected to the first pump element and the second pump element, and operable to selectively provide power to the first pump element and the second pump element;
    wherein, the first pump element expands when power is provided to the first pump element to increase pressure in the first volume to pump the working fluid from the first volume into the first rolling bladder and the second rolling bladder such that the first rolling bladder and the second rolling bladder expand to the extended state; and
    wherein, the second pump element expands when power is provided to the second pump element to increase pressure in the second volume to pump working fluid from the second volume into the accumulator and retracts when power is removed from the second pump element such that fluid drains from the first rolling bladder and the second rolling bladder into the second volume and the first rolling bladder and the second rolling bladder retract to the retracted state.

16. The system of claim 15, further comprising:
a first check valve positioned between the first volume and the first rolling bladder and the second rolling bladder and configured to control flow of working fluid from the first volume to the first rolling bladder and the second rolling bladder;
a second check valve positioned between the first volume and the accumulator and configured to control flow of working fluid between first volume and the accumulator;
a third check valve positioned between the second volume and the first rolling bladder and the second rolling bladder and configured to control flow of working fluid from the first rolling bladder and the second rolling bladder to the second volume; and
a relief valve position between the second volume and the accumulator and configured to control flow of working fluid from the second volume to the accumulator.

17. The system of claim 16, wherein the first check valve allows working fluid to flow from the first volume to the first rolling bladder and the second rolling bladder when the first pump element expands and prevents working fluid from flowing back into the first volume when the first pump element retracts after power is removed.

18. The system of claim 16, wherein the second check valve allows working fluid to flow from the accumulator into the first volume when the first pump element retracts after power is removed.

19. The system of claim 16, wherein the relief valve is configured to allow working fluid to flow from the second volume to the accumulator when the second pump element expands when power is applied to the second pump element.

20. The system of claim 16, wherein the third check valve is configured to allow the working fluid to flow from the first rolling bladder and the second rolling bladder to the second volume such that the first rolling bladder and the second rolling bladder return to the retracted state when the second pump element retracts after power is removed.

21. The system of claim 20, further comprising power source circuitry configured to selectively provide power to one of the first pump element and the second pump element.

22. The system of claim 21, wherein the power supply source circuitry comprises:
a first diode positioned between the wire coil and the first pump element such that power is provided to the first pump element when current is induced in the wire coil using a rectified sinusoidal signal having a first polarity; and
a second diode positioned between the wire coil and the second pump element such that power is provided to the second pump element when current is induced in the wire coil using a rectified sinusoidal signal having a second polarity, opposite the first polarity.

23. The system of claim 15, wherein the power source is a wire coil.

24. A spinal adjustment system comprising:
a first rolling bladder configured expand from a retracted state to an extended state and from the extended state to the retracted state;
a first pump in fluid communication with the first rolling bladder and configured to provide a working fluid to the first rolling bladder such that the first rolling bladder extends to the extended state and to remove working fluid from the first rolling bladder such that the first rolling bladder retracts to the retracted state,
the first pump including:
    a first volume filled with the working fluid;
    a first pump element mounted in the first volume and operable to expand when activated to pump the working fluid out of the first volume;

a second volume filled with the working fluid;

a second pump element mounted in the second volume and operable to expand when activated to pump the working fluid out of the second volume;

wherein the first rolling bladder is in fluid communication with the first volume and the second volume and expand to the expanded state when working fluid flows into the first rolling bladder to retract when the working fluid flows out of the first rolling bladder;

an accumulator in fluid communication with the first volume and the second volume;

a power source electrically connected the first pump element and the second pump element, and operable to selectively provide power to the first pump element and the second pump element;

wherein, the first pump element expands when power is provided to the first pump element to increase pressure in the first volume to pump the working fluid from the first volume into the first rolling bladder such that the first rolling bladder expands to the extended state; and wherein, the second pump element expands when power is provided to the second pump element to increase pressure in the second volume to pump working fluid from the second volume into the accumulator and retracts when power is removed from the second pump element such that fluid drains from the first rolling bladder into the second volume and the first rolling bladder retracts to the retracted state; and a second rolling bladder configured expand from a retracted state to an extended state and from the extended state to the retracted state;

a second pump in fluid communication with the second rolling bladder and configured to provide a working fluid to the second rolling bladder such that the first rolling bladder extends to the extended state and to remove working fluid from the second rolling bladder such that the second rolling bladder retracts to the retracted state, the second pump including:

a third volume filled with the working fluid;

a third pump element mounted in the third volume and operable to expand when activated to pump the working fluid out of the third volume;

a fourth volume filled with the working fluid;

a fourth pump element mounted in the fourth volume and operable to expand when activated to pump the working fluid out of the fourth volume;

wherein the second rolling bladder is in fluid communication with the third volume and the fourth volume and expand to the expanded state when working fluid flows into the second rolling bladder to retract when the working fluid flows out of the second rolling bladder;

a second accumulator in fluid communication with the third volume and the fourth volume;

a second power source electrically connected the third pump element and the fourth pump element, and operable to selectively provide power to the third pump element and the fourth pump element;

wherein, the third pump element expands when power is provided to the third pump element to increase pressure in the third volume to pump the working fluid from the third volume into the second rolling bladder such that the second rolling bladder expands to the extended state; and wherein, the fourth pump element expands when power is provided to the fourth pump element to increase pressure in the fourth volume to pump working fluid from the fourth volume into the second accumulator and retracts when power is removed from the fourth pump element such that fluid drains from the second rolling bladder into the fourth volume and the second rolling bladder retracts to the retracted state.

\* \* \* \* \*